United States Patent
Besemer et al.

(10) Patent No.: US 7,491,862 B1
(45) Date of Patent: Feb. 17, 2009

(54) ALKALI-NEUTRALISING SUPERABSORBENT PRODUCTS

(75) Inventors: Arie Besemer, Amerongen (NL); Anne Mieke Verwilligen, Zeist (NL); Jeffrey Thornton, Huizen (NL)

(73) Assignee: SCA Hygiene Products Zeist B.V., Zeist (NL)

( * ) Notice: Subject to any disclaimer, the term of this patent is extended or adjusted under 35 U.S.C. 154(b) by 1063 days.

(21) Appl. No.: 10/111,753

(22) PCT Filed: Nov. 3, 2000

(86) PCT No.: PCT/NL00/00797

§ 371 (c)(1),
(2), (4) Date: Apr. 30, 2002

(87) PCT Pub. No.: WO01/32226

PCT Pub. Date: May 10, 2001

(30) Foreign Application Priority Data

Nov. 3, 1999 (EP) .................................. 99203622

(51) Int. Cl.
*A61F 13/15* (2006.01)
(52) U.S. Cl. ....................... 604/359; 604/367; 604/360; 604/364
(58) Field of Classification Search ................. 604/359, 604/360, 364, 367
See application file for complete search history.

(56) References Cited

U.S. PATENT DOCUMENTS

| 3,707,148 | A |   | 12/1972 | Bryce |
|---|---|---|---|---|
| 3,794,034 | A |   | 2/1974 | Jones |
| 4,093,776 | A | * | 6/1978 | Aoki et al. ................... 428/402 |
| 4,583,980 | A |   | 4/1986 | Schneider et al. |
| 4,734,478 | A | * | 3/1988 | Tsubakimoto et al. ...... 527/300 |
| 4,842,593 | A | * | 6/1989 | Jordan et al. ................ 604/360 |
| 5,137,537 | A |   | 8/1992 | Herron et al. |
| 5,599,335 | A | * | 2/1997 | Goldman et al. ............ 604/368 |
| 6,245,693 | B1 | * | 6/2001 | Gagliardi et al. .............. 442/76 |
| 6,462,252 | B1 |   | 10/2002 | Runeman et al. |

FOREIGN PATENT DOCUMENTS

| EP | 0 316 518 B1 | 8/1988 |
|---|---|---|
| EP | 0 311 344 A2 | 12/1989 |
| EP | 0 761 241 A2 | 3/1997 |
| WO | 95/19191 | 7/1995 |
| WO | 95/22655 | 8/1995 |

* cited by examiner

*Primary Examiner*—Jacqueline F. Stephens
(74) *Attorney, Agent, or Firm*—Buchanan Ingersoll & Rooney PC

(57) ABSTRACT

A superabsorbent article of the invention having improved odour control and microbial control, comprises a liquid-impervious back layer, a liquid-absorbing intermediate layer containing a partially neutralized, acidic hydrophilic polymer, especially a surface-crosslinked polyacrylate, and a liquid-pervious, non-absorbing top layer, and is characterised by comprising an alkali-neutralising agent which is evenly distributed in said absorbing intermediate layer.

13 Claims, No Drawings

ALKALI-NEUTRALISING SUPERABSORBENT PRODUCTS

The present invention relates to a superabsorbent article, which has enhanced odour control and prevents bacterial growth, and to a method of producing such an article.

Superabsorbent materials for use in baby diapers, feminine hygiene products and incontinence pads of various types are known in the art. They usually contain a strongly hydrophilic crosslinked polymer of the partially neutralised polyacrylate type. A problem of such hydrophilic particles, however, is that the granular polymers have a tendency to clump, "gel block", which reduces inter-particle porosity and limits the swelling, rate. Therefore, many superabsorbent materials are nowadays of an advanced type, i.e. with additional surface-crosslinking resulting in improved dispersibility and increased absorption rate. The surface crosslinking can be effected with e.g. diglycidyl compounds or alkylene carbonates at high temperature. It results in membrane-like surface properties and hence in enhanced water transport (swelling behaviour) and in better mechanical properties (higher absorption under load) (for a review, see e.g. Buchholz and Graham, *Modern Superabsorbent Polymer Technology*, Wiley—VCH, 1998, especially Ch. 3: *Commercial processes for the manufacture of superabsorbent polymers* and Ch. 5: *The structure and properties of superabsorbent polyacrylates*, and references cited therein).

A problem related to the use of superabsorbent materials is the odour caused by urine components, especially ammonia and other alkaline nitrogen-containing compounds. These components cause superabsorbent materials to become objectionable long before their maximum absorbing capacity has been used. Also bacterial growth may lead to products that are odorous and/or irritating to the skin. Consequently, there is a need for superabsorbent materials, which have odour control and reduced bacterial growth when contacted with body fluids, while retaining the effective absorption and dispersibility of the "modern" superabsorbent polymers.

It has been proposed to incorporate pH controlling agents or ammonia absorbing agents into diapers to reduce the odour and bacterial growth problems and skin irritation ("diaper rash"). EP-A-202,127 discloses absorbent articles of the first generation type (not surface-crosslinked) on the basis of particulate, highly (>50%, especially >65%) neutralised polyacrylate, in which about 10% by weight of polymeric pH control agents such as non-neutralised polyacrylic acid, cellulose phosphate are non-uniformly distributed in discrete zones of the absorbent article. Non-polymeric pH controlling agents such as citric acid are also claimed, but are not illustrated in EP-202,127. The non-uniform distribution means that some zones should have a high acid/absorbent ratio of at least 10/1, while other zones should have a low acid/absorbent ratio of no more than 1/10. It is stated that the non-uniform distribution is necessary as simple combination of the pH control agents with the superabsorbent polymer in the same structure cannot be accomplished without difficulty, i.e. only with considerable lowering of the absorption capacity.

EP-A-311,344 discloses incontinence absorbent articles for reducing diaper rash, which contain an antimicrobial agent and a pH buffering agent which together keep the pH of absorbed bicarbonate-containing, *Proteus vulgaris*-contaminated urine at below 7.5. The buffering agent is partly neutralised acrylate or another acid.

It was surprisingly found now that an effective odour control can be achieved by evenly distributing a low molecular weight alkali-neutralising (pH controlling) compound in the absorbent article, while retaining the high absorptive power of non-acidic absorbent polymers, including the surface-crosslinked types. Thus the invention pertains to a superabsorbent article having improved odour control and microbial control, comprising a liquid-impervious back layer, a liquid-absorbing intermediate layer containing a partially neutralised acidic hydrophilic polymer, and a liquid-pervious, non-absorbing top layer, and further comprising an alkali-neutralising agent, wherein the alkali-neutralising agent is distinguished from the partially neutralised acidic hydrophilic polymer and is evenly distributed in said absorbing intermediate layer.

The superabsorbent polymer may be any type of hydrophilic polymer, typically on the basis of synthetic polymers of unsaturated carboxylic acids, such as polyacrylate and/or polymaleate. The superabsorbent polymer is preferably surface-crosslinked, i.e. of the type having particles with distinct relatively rigid outer layer layers and relatively weak, high-swelling internal gel bodies. The superabsorbent polymer is preferably not acidic itself, i.e. is highly neutralised in case of acidic polymers and—without the alkali-neutralising agent—has a pH above 5, especially above 5.5, more especially above 5.8, upon wetting, in order to have sufficient absorptive capacity. Therefore, the acidic polymer has a degree of neutralisation of at least 50%, especially between 60 and 80%.

Suitable alkali-neutralising (acidifying) agents include organic di- or poly-carboxylic acid acids such as maleic, fumaric, oxalic, malonic, succinic, and similar acids, and especially hydroxyacids such as citric, gluconic, ascorbic, glycolic, glyceric, lactic, malic, tartaric, salicylic acid and the like, as well as benzoic acid and phosphoric and other inorganic acids. These acids may be used in combination with their partially neutralised salts (e.g. monosodium citrate or monopotassium phosphate) to provide buffering capacity. Also, neutral materials ("hidden acids"), especially internal esters and anhydrides of the acids can be incorporated for lowering the pH. These include acid lactides (lactide, glycolide), anhydrides, e.g. maleic anhydride, succinic anhydride, and $\gamma$- and $\delta$-lactones, such as gluconolactone. These lactides, anhydrides and lactones can act in two ways: they can hydrolyse to produce a neutralising acid, or they can react with an amine to produce an amide; either way results in eliminating the amines and other undesired components. The type and the amount of the alkali-neutralising agents should be such that the pH of the absorbent layer, when wetted is 5.6 or lower, down to e.g. pH 3.5, preferably between 5.0 and 4.0.

The alkali-neutralising agents can also be present in slow-release form such as capsules, granules or small tablets with a slowly dissolving layer of e.g. linear dextrins or other slowly dissolving material. Such capsules, granules or small tablets may have dimensions of e.g. 50-250 μm and are evenly distributed through the absorbing material.

The absorption capacity can be expressed as free swelling capacity (FSC) and the centrifugal retention capacity (CRC), and with the absorption under load (AUL), or with other suitable parameters, using a modified synthetic urine (SU) as test liquid. The composition of this synthetic urine, which simulates urine also in that it is buffered, is as follows: 300 mM urea, 60 mM KCl, 130 mM NaCl, 2.0 mM $CaSO_4$, 3.5 mM $MgSO_4$, 29 mM $KH_2PO_4$, 5.3 mM $Na_2HPO_4$, 1 mg/l Triton X-100 in deionised water.

The superabsorbent articles of the invention can be used for absorbing liquids, especially of body fluids containing various salts and non-ionic substances, together with alkaline and/or malodorous components. The articles are particularly suitable in the form of absorbent hygiene articles, such as diapers, sanitary towels, incontinence pads and the like. Such articles can be produced entirely on the basis of the single superabsorbent polymers such as polyacrylates and polymaleates, but they can also contain a mixture of absorbent materials, such as different polyacrylates, cellulose derivatives and other polysaccharides.

The absorbent article is preferably a layered product, in which the superabsorbent polymer constitutes at least one layer. The absorbent layer can be located between a liquid-pervious top layer and a liquid-impervious bottom layer. In particular the product may have four layers. The first one can be a thin, non-woven layer of polyester fibres or other fibres. The second layer can be a wadding which is used for acquiring and spreading the absorbed fluid such as urine. The third layer can consist of fluff pulp wherein the superabsorbent polymer is spread as fine particles, especially 50-800 μm. The last layer can be a back sheet of a water-resistant material such as polyethylene, which prevents leakage from the layered absorption product. The product may instead have three layers, in which the fluff layer and the absorbent layer are combined. In either form, the neutralising compound is evenly distributed with the superabsorbent polymer through the fluff.

EXAMPLE 1

Sanitary towels having an upper core and a lower core and a size of 10*28 cm were produced. The upper core contained MS CTMP pulp (350 g/m$^2$) and 15 wt. % of super-absorbent polymer (SAP), the lower core contained KEA pulp (310 g/m$^2$) and 21 wt. % of SAP. Thus, the total weight of the cores is (0.10*0.28*350*1.15)+(0.10*0.28*310*1.21)g=21.8 g. The bulk volume was 8 cm$^3$/g. The SAP was either highly neutralised polyacrylate (IM7100) or acidic (30% neutralised) polyacrylate (IM7110). IM7100 has a better absorptive power than IM7110. To the SAP, an acid was added in the amounts given below. Gluconic acid was added as a 50% (w/w) solution, citric acid was added as a powder or a crushed tablet. The towel was contacted with modified synthetic urine (SU, see above). The absorption capacity (AC) was measured in g of liquid absorbed by the towel per g of product (superabsorbent polymer plus pulp). The towel is placed on a 300 inclined Perspex test plate, the lower 2-3 cm being immersed in the test liquid (SU). The acquisition time (AT) was measured as the time needed to take up 50 ml of the test liquid per towel and was measured three times consecutively. The results are given below.

| SAP | Acid | Amount (mmoles) | pH (wet) | AC (g/g) | AT (sec) |
|---|---|---|---|---|---|
| IM7100 | — | — | 5.9 | 11.4 | 14, 14, 20 |
| IM7110 | — | — | 5.0 | 10.5 | 19, 21, 32 |
| IM7100 | Gluconic | 1.9 | 5.6 | 11.3 | |
| IM7100 | Gluconic | 3.9 | 5.2 | 11.1 | |
| IM7100 | Gluconic | 5.6 | 5.0 | 10.8 | |
| IM7100 | Gluconic | 6.9 | 4.8 | 10.4 | |
| IM7100 | Gluconic | 9.1 | 4.3 | 10.5 | |
| IM7100 | Citric* | 6.2 | 4.7 | 11.5 | 14, 15, 21 |
| IM 7100 | Citric* | 8.3 | 4.3 | 11.4 | 14. 16, 21 |
| IM 7100 | Citric* | 10.4 | 4.0 | 10.9 | 15, 17, 24 |

*added as powder

The invention claimed is:

1. A superabsorbent article having improved odour control and microbial control, comprising a liquid-impervious back layer, a liquid-absorbing intermediate layer containing a surface-crosslinked, partially neutralized, acidic hydrophilic polymer, and a liquid-pervious, non-absorbing top layer, wherein a low molecular weight alkali-neutralizing agent is evenly distributed in said absorbing intermediate layer, which alkali-neutralizing agent is distinguished from the partially neutralized, acidic hydrophilic polymer, and said absorbing layer, after humidification with neutral water, has a pH of 5.6 or lower, wherein the acidic polymer has a degree of neutralization of at least 50%.

2. A superabsorbent article according to claim 1, in which the alkali neutralizing agent is an organic acid selected from maleic, fumaric, oxalic, malonic, succinic, citric, gluconic, ascorbic, glycolic, glyceric, lactic, malic, tartaric and salicylic acid.

3. A superabsorbent article according to claim 2, in which the alkali neutralizing agent is selected from citric, malic and lactic acid.

4. A superabsorbent article according to claim 1, in which the alkali neutralizing agent is selected from anhydrides, lactides and lactones.

5. A superabsorbent article according to claim 4, in which the alkali neutralizing agent is selected from dilactide, glycolide, butyrolactone, valerolactone, gluconolactone and maleic anhydride.

6. A superabsorbent article according to claim 1, in which the alkali neutralizing agent is present in amount of 0.2 to 1 weight part per weight part of hydrophilic polymer.

7. A superabsorbent article according to claim 1, in which the article contains a cellulosic carrier material in an amount of 2 to 10 weight parts per weight part of hydrophilic polymer.

8. A superabsorbent article according to claim 1, in which the hydrophilic polymer comprises polyacrylate.

9. A superabsorbent article according to claim 1, which contains 2.5 to 10 g of hydrophilic polymer.

10. A superabsorbent article according to claim 1, in which the acidic polymer has a degree of neutralization of between 60 and 80%.

11. A process for producing a superabsorbent article having improved odor control and microbial control, comprising
   mixing a low molecular weight alkali-neutralizing agent with surface-crosslinked, highly neutralized acidic hydrophilic polymer, distributing the mixture in a fibrous carrier material, which alkali-neutralizing agent is distinguished from the partially neutralized, acidic hydrophilic polymer, the alkali-neutralizing agent being mixed in an amount which ensures a pH of 5.6 or lower in the layer of carrier material after humidification with neutral water,
   working the carrier material into a layer and
   covering the layer of carrier material with a liquid-impervious layer on one side and with a liquid-impervious, non-absorbing layer, at the other side,
   wherein the acidic polymer has a degree of neutralization of at least 50%.

12. A superabsorbent article having improved odour control and microbial control, comprising a liquid-impervious back layer, a liquid-absorbing intermediate layer containing a surface-crosslinked, partially neutralized, acidic hydrophilic polymer, and a liquid-pervious, non-absorbing top layer,
   wherein an alkali-neutralizing agent selected from organic dicarboxylic acids, polycarboxylic acids, hydroxyacids, lactides, anhydrides, and lactones is evenly distributed in said absorbing intermediate layer, and said absorbing layer, after humidification with neutral water, has a pH between 3.5 and 5.0.

13. A process for producing a superabsorbent article having improved odor control and microbial control, comprising mixing an alkali-neutralizing agent with surface-crosslinked, highly neutralized acidic hydrophilic polymer, distributing the mixture in a fibrous carrier material, working the carrier material into a layer and covering the layer of carrier material with a liquid-impervious layer on one side and with a liquid-impervious, non-absorbing layer, at the other side, the alkali-neutralizing agent being selected from organic dicarboxylic acids, polycarboxylic acids, hydroxyacids, lactides, anhydrides, and lactones, and the alkali-neutralizing agent being mixed in an amount which ensures a pH between 3.5 and 5.0 in the layer of carrier material after humidification with neutral water.

* * * * *